United States Patent
Anderson et al.

(10) Patent No.: US 10,131,799 B2
(45) Date of Patent: Nov. 20, 2018

(54) ANTIFOULING COATING COMPOSITION AND ITS USE ON MAN-MADE STRUCTURES

(71) Applicant: Akzo Nobel Coatings International B.V., Arnhem (NL)

(72) Inventors: Colin Dudgeon Anderson, Newcastle Upon Tyne (GB); Scott Paul Thompson, Newcastle Upon Tyne (GB); Frank Lasasso, Hazlet, NJ (US); Kate Moss, Stockbridge (GB)

(73) Assignee: AKZO NOBEL COATINGS INTERNATIONAL B.V., Arnhem (NL)

( * ) Notice: Subject to any disclaimer, the term of this patent is extended or adjusted under 35 U.S.C. 154(b) by 183 days.

(21) Appl. No.: 15/110,334

(22) PCT Filed: Jan. 6, 2015

(86) PCT No.: PCT/EP2015/050077
§ 371 (c)(1),
(2) Date: Jul. 7, 2016

(87) PCT Pub. No.: WO2015/106984
PCT Pub. Date: Jul. 23, 2015

(65) Prior Publication Data
US 2016/0326379 A1 Nov. 10, 2016

Related U.S. Application Data

(60) Provisional application No. 61/964,869, filed on Jan. 16, 2014.

(30) Foreign Application Priority Data

Jan. 30, 2014 (EP) .................................... 14153265

(51) Int. Cl.
| | |
|---|---|
| C09D 5/16 | (2006.01) |
| A01N 43/36 | (2006.01) |
| A01N 59/20 | (2006.01) |
| A01N 25/10 | (2006.01) |
| A01N 25/34 | (2006.01) |
| B05D 1/02 | (2006.01) |
| B63B 59/04 | (2006.01) |
| A01N 59/16 | (2006.01) |

(52) U.S. Cl.
CPC ........... *C09D 5/1668* (2013.01); *A01N 25/10* (2013.01); *A01N 25/34* (2013.01); *A01N 43/36* (2013.01); *A01N 59/16* (2013.01); *A01N 59/20* (2013.01); *B05D 1/02* (2013.01); *B63B 59/04* (2013.01); *C09D 5/16* (2013.01); *C09D 5/1606* (2013.01); *C09D 5/1625* (2013.01)

(58) Field of Classification Search
CPC .... C09D 5/1625; C09D 5/1668; B63B 59/04; A01N 43/36; A01N 59/20
USPC ......................................................... 523/122
See application file for complete search history.

(56) References Cited

U.S. PATENT DOCUMENTS

| | | | |
|---|---|---|---|
| 6,069,189 A | 5/2000 | Kramer et al. | |
| 2008/0293848 A1 | 11/2008 | Tomko et al. | |

FOREIGN PATENT DOCUMENTS

| | | |
|---|---|---|
| EP | 0 204 456 A1 | 12/1986 |
| EP | 0 342 276 A1 | 11/1989 |
| EP | 0 779 304 A1 | 6/1997 |
| EP | 0 831 134 A1 | 3/1998 |
| EP | 2 551 309 A1 | 1/2013 |
| GB | 1 457 590 A | 12/1976 |
| WO | 96/03465 A1 | 2/1996 |
| WO | 03/039256 A1 | 5/2003 |
| WO | 05/005516 A1 | 1/2005 |
| WO | 05/075581 A1 | 8/2005 |
| WO | 05/075582 A1 | 8/2005 |
| WO | 07/088172 A1 | 8/2007 |
| WO | 07/088172 A2 | 8/2007 |
| WO | 07/103013 A2 | 9/2007 |
| WO | 07/116051 A1 | 10/2007 |

OTHER PUBLICATIONS

Extended European Search Report issued in corresponding European Application No. 14153265.5 dated Jun. 23, 2014, 9 pages.

*Primary Examiner* — Fred M Teskin
(74) *Attorney, Agent, or Firm* — McDonnell Boehnen Hulbert & Berghoff LLP

(57) ABSTRACT

The invention pertains to an antifouling coating composition comprising a copper acrylate polymer, 2-(p-chlorophenyl)-3-cyano-4-bromo-5-trifluoromethyl pyrrole (tralopyril), and solvent, with the coating composition being substantially free of further biocidal compounds, wherein the copper acrylate polymer is present in an amount of 60-99 wt. % and the tralopyril is present in an amount of 0.1-30 wt. %, the weight percentages for copper acrylate polymer and tralopyril being calculated on the dry weight of the coating composition. In one embodiment, the coating composition comprises 30-70 wt % of solvent, the weight percentage of solvent being calculated on the wet weight of the coating composition. It has been found that the coating composition according to the invention combines a good antifouling performance against both weed and shell fouling, for at least 12 months, i.e. a yacht season, with a high gloss finish, and, when a suitable application method is used, a smooth and level surface.

19 Claims, No Drawings

ANTIFOULING COATING COMPOSITION AND ITS USE ON MAN-MADE STRUCTURES

This application is a US national phase of international application PCT/EP2015/050077, filed Jan. 6, 2015, which claims priority to U.S. Provisional Application No. 61/964,869, filed Jan. 16, 2014 and European Application No. 14153265.5, filed Jan. 30, 2014.

This invention pertains to an antifouling coating composition with desirable properties, which is suited as coating on man-made structures immersed in an aquatic environment. The invention also pertains to a process for protecting a man-made structure immersed in a fouling aquatic environment using an antifouling coating composition according to the invention, and to a man-made structure immersed in a fouling aquatic environment coated with an antifouling coating composition according to the invention.

Man-made structures such as ship- and boat hulls, buoys, drilling platforms, oil production rigs, and pipes which are immersed in water are prone to fouling by aquatic organisms such as green and brown algae, barnacles, mussels, and the like. Such structures are commonly of metal, but may also comprise other structural materials such as wood, fibre-glass or concrete. This fouling is a nuisance on boat hulls, because it increases frictional resistance during movement through the water, the consequence being reduced speeds and increased fuel costs. It is a nuisance on static structures such as the legs of drilling platforms and oil production rigs, firstly because the resistance of thick layers of fouling to waves and currents can cause unpredictable and potentially dangerous stresses in the structure, and, secondly, because fouling makes it difficult to inspect the structure for defects such as stress cracking and corrosion. It is a nuisance in pipes such as cooling water intakes and outlets, because the effective cross-sectional area is reduced by fouling, with the consequence that flow rates are reduced. An antifouling coating composition will generally be applied as a top-coat on immersed areas of the structure to inhibit the settlement and growth of aquatic organisms such as barnacles and algae, generally by the release of a biocide for the aquatic organisms.

Traditionally, antifouling coating compositions have comprised a relatively inert binder with a biocidal pigment that is leached from the coating composition.

Among the binders which have been used are vinyl resins and rosin or rosin derivatives. Vinyl resins are water-insoluble and coating compositions based on them use a high pigment concentration so as to have contact between the pigment particles to ensure leaching. Rosin is a hard brittle resin that is very slightly soluble in water. Rosin-based antifouling coating compositions have been referred to as soluble matrix or ablating coating compositions. The biocidal pigment is very gradually leached out of the matrix of rosin binder in use, leaving a skeletal matrix of rosin, which becomes washed off the hull surface to allow leaching of the biocidal pigment from deep within the coating composition film.

Many successful antifouling coating compositions in recent years have been "self-polishing copolymer" coating compositions based on a polymeric binder to which biocidal tri-organotin moieties are chemically bound and from which the biocidal moieties are gradually hydrolysed in an aquatic environment. In such binder systems, the side groups of a linear polymer unit are split off in a first step by reaction in the aqueous medium, the polymer framework that remains becoming water-soluble or water-dispersible as a result. In a second step, the water-soluble or water-dispersible framework at the surface of the coating composition layer on the ship is washed out or ablated. Such coating composition systems are described for example in GB-A-1 457 590.

As the use of tri-organotin has been prohibited worldwide, there is a need for alternative antifouling substances that can be used in antifouling compositions.

Various alternative antifouling compositions which do not contain tri-organotin have been described in the art.

WO2005/005516 describes an antifouling coating composition which comprises a silyl ester copolymer, and an ingredient having biocidal properties for aquatic organisms.

WO2005/075582 describes an antifouling coating composition which comprises a film-forming polymer with an acrylic backbone in combination with a copper-based biocide.

U.S. Pat. No. 6,069,189 describes a light- and bright-colored antifouling paint comprising a barnaclecide in combination with an algicide. In one embodiment copper acrylate is described as film-forming polymer. The barnaclecide preferably is 2-trifluoromethyl-3-bromo-4-cyano-5-parachlorophenyl pyrrole. Seanine, Irgarol 1051, and Preventol A4S are used as algicide.

It has been found very difficult to obtain a coating which combines a good antifouling performance against both weed and shell fouling, for at least 12 months, i.e. a yacht season, with a high gloss finish, and preferably a smooth and level surface. It has been found that this can be solved by the provision of a coating with a very specific composition.

The invention pertains to an antifouling coating composition comprising a copper acrylate polymer, 2-(p-chlorophenyl)-3-cyano-4-bromo-5-trifluoromethyl pyrrole (tralopyril), and solvent, with the coating composition being substantially free of further biocidal compounds, wherein the copper acrylate polymer is present in an amount of 60-99 wt. % and the tralopyril is present in an amount of 0.1-30 wt. %, the weight percentages for copper acrylate polymer and tralopyril being calculated on the dry weight of the coating composition.

In one embodiment, the coating composition comprises 30-80 wt % of solvent, the weight percentage of solvent being calculated on the wet weight of the coating composition.

In the present specification, the wording "calculated on the dry weight of the coating composition" means that the calculation is based on the coating composition excluding the solvent. On the other hand, the wording "calculated on the wet weight of the coating composition" means that the calculation is based on the coating composition including the solvent.

The term solvent encompasses comprises those ingredients which are liquid at 0-50° C., which are not reactive with the copper acrylate polymer and which possess a vapour pressure of more than 0.01 kPa at 25° C. or a boiling point of below 250° C. at 1 atmosphere pressure.

It has been found that the coating composition according to the invention combines a good antifouling performance against both weed and shell fouling, for at least 12 months, i.e. a yacht season, with a high gloss finish, and, when a suitable application method is used, a smooth and level surface.

The invention will be discussed in more detail below.

The compound 2-(p-chlorophenyl)-3-cyano-4-bromo-5-trifluoromethyl pyrrole is a biocide known as tralopyril. It is commercially available under the trade name Econea. It is known as a barnaclecide. It has been found that the use of a copper acrylate polymer in combination with tralopyril as biocide, with the composition not containing further biocides, makes for a coating composition which shows good anti-fouling performance, not only against shell fouling for which tralopyril is known to be effective, but also against fouling with weed. Additionally, the coating composition according to the invention has a predictable life, dissolving away at a constant rate to give at least 12 months performance. Additionally, the coating according to the invention shows high gloss, and, depending on the application method, shows a very smooth and level surface.

The addition of further biocides, in particular zinc pyrithione, has been found to detrimentally affect the properties of the coating. Therefore, the coating composition according to the invention is substantially free of further biocidal components. If this requirement is not met, the advantageous effects of the present invention are not obtained. In the context of the present invention the indication substantially free of means that the component in question is not present in such an amount that the properties of the coating composition are detrimentally affected. Within the framework of the present application, a biocidal compound is a compound that is used in an antifouling coating composition to provide a biocidal effect on aquatic fouling organisms.

For the present specification this means that the coating composition comprises less than 1 wt. % of other biocides than tralopyril, more preferred the coating composition comprises less than less than 0.1 wt. % of other biocides than tralopyril, the wt. % being calculated based upon the total content of the coating composition. In one embodiment, the coating composition is free from further biocidal components.

An additional feature of the present invention is that the composition according to the invention can be obtained with a low pigment volume concentration. This makes for a glossy smooth surface.

In one embodiment, the pigment volume concentration (PVC) is less than 30%, in particular less than 20%, more in particular less than 15%, still more in particular less than 10%. It may be possible for the PVC to be lower, e.g., less than 7%, or less than 5%.

The composition according to the invention comprises 0.1-30 wt. % of tralopyril, calculated on the dry weight of the coating composition. When the amount of tralopyril is below 0.1 wt. %, the antifouling effect of the present invention will not be obtained. When the amount of tralopyril is too high, no additional antifouling effect will be obtained, while the cost of the coating composition will be increased and the further performance may be affected. To obtain an effective coating composition it may be preferred for the amount of tralopyril to be at least 0.5 wt. %, in particular at least 1 wt. %, more in particular at least 2 wt. %, still more in particular at least 4 wt. %. On the other hand, to balance the cost and properties of the coating composition, it may be preferred for the amount of tralopyril to be at most 20 wt. %, in particular at most 15 wt. %, more in particular at most 12 wt. %, even more in particular at most 10 wt. %.

The coating composition according to the invention comprises 60-99 wt. % of a copper acrylate polymer, calculated on the dry weight of the coating composition. It may be preferred for the composition to comprise at least 70 wt. % of the copper acrylate polymer, in particular at least 75 wt. %, more in particular at least 85 wt. %. The maximum content of copper acrylate polymer is determined by the minimum amount of other components, and may be at most 98 wt. %, or at most 96 wt. %.

In one embodiment, the coating composition according to the invention comprises 30-80 wt. % of solvent. Where the amount of solvent is very low, obtaining a coating with high gloss and, depending on the application method, a smooth and level surface may be difficult. The addition of very high amounts of solvents is not advantageous, because it entails large volumes of material which will not end up in the final coating composition. It may be preferred for the coating composition to comprise at least 40 wt. % of solvent, in particular at least 50 wt. %, more in particular at least 55 wt. %. It may also be preferred for the amount of solvent to be at most 75 wt. %, in particular at most 70 wt. %, more in particular at most 65 wt. %. The solvent content is calculated on the wet weight of the coating composition.

In one embodiment, the composition contains 0-15 wt. % of further components, calculated on the wet weight of the coating composition, wherein further components are all compounds which are not solvent, copper acrylate polymer, and tralopyril. It may be preferred for the composition to comprise 0-10 wt. % of further compounds, in particular 0-5 wt. %, calculated on the wet weight of the coating composition.

In one embodiment, the present invention pertains to a coating composition comprising 60-99 wt. % of a copper acrylate polymer, in particular 70-98 wt. %, more in particular 78-98 wt. %, and 2-30 wt. % of tralopyril, in particular 2-15 wt. %, more in particular 2-10 wt. %, still more in particular 4-10 wt. %, wherein the percentages of copper acrylate polymer and tralopyril are calculated on the dry weight of the coating composition, and 40-80 wt. % of solvent, in particular 50-70 wt. % of solvent, more in particular 55-65 wt. % of solvent, and 0-15 wt. % of further compounds, in particular 0-10 wt. %, more in particular 0-5 wt. %, wherein the percentages of solvent and other components are calculated on the wet weight of the coating composition, with the coating composition being substantially free of further biocidal compounds.

In the coating composition according to the invention, a copper acrylate polymer is used. Copper acrylate polymers suitable for use in coating compositions are known in the art. They encompass copper and an acrylic backbone. Suitable copper acrylates for use in antifouling coating compositions, are, e.g., described in EP204456 and EP0779304 to Nippon Paint, and WO2005/075582 to Akzo Nobel Coatings International.

In one embodiment, the copper acrylate polymer is a compound comprising an acrylic backbone bearing at least one terminal group of the formula:

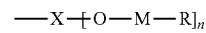

wherein X represents

M is copper, n is an integer of 1 to 2; R represents an organic residue selected from

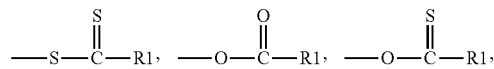

-continued

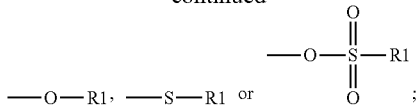

and R1 is a monovalent organic residue.
In a preferred embodiment, X is

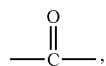

and R represents

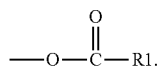

The parent acrylic polymer having a —COOH group in place of —X—[O-M-R]$_x$ preferably has an acid value of 25-350 mg KOH/g. Such hydrolysable polymers can be prepared by the processes of EP-A-204456 and EP-A-342276. Most preferably the hydrolysable polymer has a copper content of 0.3-20% by weight.

The copper acrylate polymer is preferably a copolymer comprising an acrylic or methacrylic ester whose alcohol residue includes a bulky hydrocarbon radical or a soft segment, for example a branched alkyl ester having 4 or more carbon atoms or a cycloalkyl ester having 6 or more atoms, a polyalkylene glycol monoacrylate or monomethacrylate optionally having a terminal alkyl ether group or an adduct of 2-hydroxyethyl acrylate or methacrylate with caprolactone, as described in EP-A-779304.

It is preferred for R to be the residue of an organic monobasic carboxylic acid which has a boiling point greater than 115° C. and an acid value between 50 and 950 mg KOH/gram, in particular between 100 and 300 mg KOH/gram, more in particular between 150 and 250 mg KOH/gram. There is no particular upper limit on the boiling point and R may be the residue of a substantially non-volatile acid. The material will generally have a boiling or decomposition temperature below 500° C. The organic monobasic carboxylic acid may be referred to as a high-boiling acid. The acid may be aliphatic, aromatic, linear, branched, alicyclic or heterocyclic. It is particularly preferred for R to be the residue of one or more of the following acids: benzoic acid, salicylic acid, 3,5-dichlorobenzoic acid, lauric acid, stearic acid, nitro-benzoic acid, linoleic acid, ricinoleic acid, 12-hydroxy stearic acid, fluoroacetic acid, pulvic acid, O-cresotinic acid, naphthol-1-caboxylic acid, p-oxy-benzoic acid, chloroacetic acid, dichloroacetic acid, naphthenic acid, p-phenyl benzoic acid, lithocholic acid, phenoxy acetic acid, 2,4-dichlorophenoxy acetic acid, oleic acid, versatic acid, nicotinic acid, penicillic acid and the like, or a diterpenoid acid having an abietane, pimarane, isopimarane or labdane skeleton such as, for example, abietic acid, neoabietic acid, levopimaric acid, dextropimaric acid, sandaracopimaric acid, and the like which may be used individually or in combination.

In one embodiment, a copper acrylate is used which can be prepared as follows:
i) polymerization of an unsaturated organic acid monomer and an additional unsaturated monomer and either reacting the resulting acrylic resin with a metal compound and a monobasic acid or reacting said acrylic resin with a metal salt of a monobasic acid or
ii) reacting an unsaturated organic acid monomer with a metal compound and a monobasic acid or reacting an unsaturated organic acid monomer with a metal salt of a monobasic acid and polymerizing the resulting metal-containing unsaturated monomer with another unsaturated monomer.

In view of the higher yield method i) is preferred.

The unsaturated organic acid monomer mentioned above can be selected from the group of unsaturated compounds having at least one carboxyl group, for example unsaturated monobasic acids such as (meth) acrylic acid; unsaturated dibasic acids and monoalkyl esters thereof, such as maleic acid inclusive of its monoalkyl esters and itaconic acid inclusive of its monoalkyl esters; unsaturated monobasic acid hydroxyalkyl ester-dibasic acid adducts, such as 2-hydroxyethyl (meth)acrylate-maleic acid adduct, 2-hydroxyethyl (meth)acrylate-phthalic acid adduct, and 2-hydroxyethyl (meth)acrylate-succinic acid adduct. In this specification, the term (meth)acrylic acid is used to mean whichever of methacrylic acid and acrylic acid.

The additional unsaturated monomer can be selected from various esters of (meth)acrylic acid, e.g. alkyl (meth)acrylates, the ester moieties of which contain 1 to 20 carbon atoms, such as methyl (meth)acrylate, ethyl (meth)acrylate, i-propyl (meth)acrylate, n-butyl (meth)acrylate, i-butyl (meth)acrylate, t-butyl (meth)acrylate, 2-ethylhexyl (meth)acrylate, lauryl (meth)acrylate and stearyl (meth)acrylate; hydroxy-containing alkyl (meth)acrylates, the ester moieties of which contain 1-20 carbon atoms, such as 2-hydroxypropyl (meth)arylate and 2-hydroxyethyl (meth)acrylate; cyclic hydrocarbon esters of (meth)acrylic acid, such as phenyl (meth)acrylate and cyclohexyl (meth)acrylate; polyalkylene glycol esters of (meth)acrylic acid, such as polyethylene glycol mono (meth) acrylate and polyethylene glycol mono (meth) acrylate with a degree of polymerization in the range of 2 to 50; $C_{1-3}$ alkoxyalkyl (meth)acrylate; (meth)acrylamide; vinyl compounds such as styrene, alpha-methylstyrene, vinyl acetate, vinyl propionate, vinyl benzoate, vinyltoluene and acrylonitrile; esters of crotonic acid; and diesters of unsaturated dibasic acids, such as maleic acid diesters and itaconic acid diesters. Of the above-mentioned esters of (meth)acrylic acid, the ester moieties are preferably alkyl groups containing 1 to 8 carbon atoms, more preferably an alkyl groups containing 1 to 6 carbon atoms. The preferred specific compounds are methyl (meth)acrylate, ethyl (meth) acrylate, butyl (meth)acrylate and cyclohexyl (meth)acrylate.

The above-mentioned unsaturated organic acid monomers and other unsaturated monomers may each be used alone or in a mixture of two or more species.

The copper acrylate polymer preferably has an acid value of 25 to 350 mg KOH/g. If the acid value is below 25 mg KOH/g, the amount of metal salt to be attached to the side chain is too low for effective antifouling and self-polishing properties. If it is above 350 mg KOH/g, the hydrolysis rate will be too high so that the service life of the antifouling coating is strongly reduced. It is preferred for the copper acrylate polymer to have an acid value in the range of 25 to 150 mg KOH/g, more specifically 60-80 mg KOH/g.

If so desired, the antifouling coating composition may comprise one or more non-biocidal pigments, and/or additives such as one or more thickening or thixotropic agents, one or more wetting agents, plasticisers, fillers, a liquid carrier such as an organic solvent, organic non-solvent or water, etc., all as conventional in the art.

As an example, as suitable plasticisers that may be used in the present invention, the following materials may be exemplified: chlorinated paraffins, and aromatic phosphate esters such as triisopropylphenyl phosphate. These materials may be used individually or in combination.

The antifouling coating composition according to the present invention additionally may comprise one or more pigments known in the art. Suitable pigments include zinc oxide, barium sulphate, calcium sulphate, dolomite, titanium dioxide, ferric oxide and organic pigments such as a phthalocyanine or azo pigment.

The coating composition can additionally contain conventional thickeners, particularly thixotropes such as silica, bentonite or polyamide wax and/or stabilisers, for example zeolites or aliphatic or aromatic amines such as dehydroabietylamine.

As discussed above, in one embodiment the coating composition according to the invention comprises a solvent. Suitable solvents are water and organic solvents. Water may be preferred for environmental reasons. Where water is used, the copper acrylate polymer will be present in the form of an emulsion, and the coating composition will contain emulsifyers as is known in the art. Organic solvents may be preferred for manufacturing reasons. Suitable organic solvents are known in the art, and include aromatic hydrocarbons such as xylene, toluene and trimethylbenzene, alcohols such as n-butanol, ether alcohols such as butoxyethanol or methoxypropanol, esters such as butyl acetate or isoamyl acetate, ether-esters such as ethoxyethyl acetate or methoxypropyl acetate, ketones such as methyl isobutyl ketone or methyl isoamyl ketone, aliphatic hydrocarbons such as white spirit, or a mixture of two or more of these solvents.

The coating composition can be manufactured by methods known in the art. In general, the method encompasses combining the various components of the coating composition in a solvent being an organic solvent or water.

The invention also pertains to a process for protecting a man-made structure immersed in a fouling aquatic environment wherein the structure is coated with an antifouling coating composition as described above.

Examples of man-made structures that can be provided with the coating according to the invention include ship and boat hulls, buoys, drilling platforms, oil production rigs, and pipes. They can be made of metal, concrete, wood, fiberglass or plastic.

The coating can be provided onto the man-made structures using methods known in the art. Examples of suitable methods include rolling, spraying, and brushing. Application though spraying is preferred, as it leads to a smoother application, resulting in higher gloss.

The coating composition of the present invention is normally applied as a topcoat on man-made structures. As such it can be applied in the normal coating scheme for new structures. However, it is also possible to use it as a topcoat in the maintenance and repair of existing structures. In one embodiment, it is provided for as a topcoat over a coating layer that contains biocidal copper and/or zinc and/or a rosin material.

The invention also pertains to a man-made structure immersed in a fouling aquatic environment coated with an antifouling coating composition according to the invention. For more details on the man-made structure and the coating composition reference is made to what is stated above.

The antifouling coating may have a thickness after curing of, e.g., 75 to 150 microns, in particular 90-120 microns.

In one embodiment, the man-made structure used in the present invention is a ship or boat hull, in particular a ship or boat hull of fiberglass or plastic.

It is noted that the embodiments of coating composition described herein may be combined with each other in manners clear to the skilled person. This applies to all properties and compositions. All embodiments and properties described for the coating are also applicable to the process for protecting man-made structures, and to the man-made structures provided therewith.

The present invention will be elucidated by the following Examples, without being limited thereto or thereby.

EXAMPLES

In the examples, tralopyril is provided as biocide, provided under the trade name Econea.

The copper acrylate resin has the following properties: It has an acrylic backbone bearing at least one terminal group of the formula I above, wherein X is

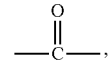

M is copper, n is 1, and R is a residue derived from naphthenic acid. The residue has an acid value of 200 mg KOH/gram. The resin has an acid value of 66-72 mg KOH/gram.

In the following, the composition of the coating is provided as weight %, calculated on the wet coating composition. The pigment volume concentration (PVC) is in volume % on the dry volume of the coating.

The indication "further ingredients" stands for thixotropes and color pigments, and in some cases co-binders such as hydrocarbon resin and/or rosin. Comparable compositions where used in coating compositions which are compared.

Example 1

This example shows the effect of the composition according to the invention, comprising only tralopyril as biocide in comparison with a composition comprising CuSCN and N'-tert-butyl-N-cyclopropyl-6-(methylthio)-1,3,5-triazine-2,4-diamine (Irgarol 1051).

Coating compositions were prepared by high-speed mixing of the constituents mentioned in table 1a.

TABLE 1a

|  | Composition 1 according to the invention | Comparative composition A |
| --- | --- | --- |
| Biocide | 7.8 wt. % Econea | 22.3 wt. % CuSCN and 2.2 wt. % Irgarol 1051 |
| Copper acrylate polymer | 31.8 wt. % | 27.6 wt. % |
| Solvent | 58.2 wt. % | 44.4 wt. % |
| Other components | 2.2 wt. % | 3.5 wt. % |
| PIGMENT VOLUME CONCENTRATION | 14.6% | 28.6% |

Panels were roller-coated with the coating composition and kept for 12 months in seawater attached to a raft located in West Palm Beach, Fla. After 12 months, the fouling coverage of the panel was determined. Table 1b gives the percentages of the panel which were, respectively clean, covered with slime, covered with weed, and covered with shells.

TABLE 1b

| | Composition 1 according to the invention | Comparative composition A |
|---|---|---|
| % clean | 99% | 10% |
| % slime | 0 | 0 |
| % weed | 0 | 0 |
| % shell | 1% | 90% |

As can be seen from Table 1 b, both compositions showed no fouling by slime and weed. However, the comparative composition suffered severely from fouling by shells, while the composition according to the invention was almost completely clean.

Example 2

This example shows the effect of the presence of tralopyril in a copper acrylate coating composition, in comparison with a composition not containing tralopyril.

Coating compositions were prepared by high-speed mixing of the constituents mentioned in table 2a.

TABLE 2a

| | Composition 2 according to the invention | Comparative composition B |
|---|---|---|
| Biocide | 1.0 wt. % Econea | 0 |
| Copper acrylate polymer | 31.0 wt. % | 31.4 wt. % |
| Solvent | 56.7 wt. % | 57.3 wt. % |
| Other components | 11.3 wt. % | 11.3 wt. % |
| PIGMENT VOLUME CONCENTRATION | 3.8% | 2.2% |

Panels were roller-coated with the coating composition and kept for 10 months in seawater at Burnham, United Kingdom. After 10 months, the fouling coverage of the panel was determined. Table 2b gives the percentages of the panel which were, respectively clean, covered with slime, covered with weed, and covered with shells.

TABLE 2b

| | Composition 2 according to the invention | Comparative composition B |
|---|---|---|
| % clean | 20% | 5% |
| % slime | 80% | 0 |
| % weed | 0 | 10% |
| % shell | 0 | 85% |

As can be seen from Table 2b, the composition according to the invention showed a 20% clean surface. The comparative composition suffered severely from fouling by shells, and additionally by some fouling by weed, and showed less clean surface than the composition according to the invention. It should also be noted that the composition according to the invention is effective at very low Pigment Volume Concentrations.

Example 3

This example compares a composition of the invention with a composition which additionally comprises zinc pyrithione.

Coating compositions were prepared by high-speed mixing of the constituents mentioned in table 3a.

TABLE 3a

| | Composition 3 according to the invention | Comparative composition C |
|---|---|---|
| Biocide | 4.0 wt. % Econea | 2.0 wt. % Econea and 2.0 wt. % Zinc pyrithione |
| Copper acrylate polymer | 17 wt. % | 17 wt. % |
| Solvent | 55 wt. % | 55 wt. % |
| Other ingredients | 24 wt. % | 24 wt. % |
| PIGMENT VOLUME CONCENTRATION | 7.72% | 7.72% |

Panels were roller-coated with the coating composition and kept for 8 months in seawater attached to a raft located in Brazilian waters. After 8 months, the fouling coverage of the panel was determined. Table 3b gives the percentages of the panel which were, respectively clean, covered with slime, covered with weed, and covered with shells.

TABLE 3b

| | Composition 3 according to the invention | Comparative composition C |
|---|---|---|
| % clean | 20% | n.d. |
| % slime | 80% | 10% |
| % weed | 0 | n.d. |
| % shell | 10% | 60% | n.d. stands for not determined.
It appeared that the comparative coating C had worn off on one-third of the panel following 8 months of immersion, making a meaningful determination of the percentages clean, slime, and weed not possible.

As can be seen from Table 3b, the composition according to the invention showed 20% clean surface, was completely free of weed and showed a lot less shell (only 10%) than comparative composition C. Further, the coating was intact and not showing any evidence of polish through. The comparative composition however polished away too fast, which makes it unsuitable for commercial use.

Example 4

Further to Example 3 above, this example investigates the effect of zinc pyrithione on the lifetime of the antifouling coating.

Coating compositions were prepared by high-speed mixing of the constituents mentioned in table 4a.

TABLE 4a

| | Composition 4 according to the invention | Comparative composition D |
|---|---|---|
| Biocide | 6.0 wt. % Econea | 6.0 wt. % zinc pyrithione |
| Copper acrylate polymer | 36.9 wt. % | 36.9 wt. % |
| Solvent | 53.0 wt. % | 53.0 wt. % |
| Other ingredients | 4.1 wt. % | 4.1 wt. % |
| PIGMENT VOLUME CONCENTRATION | 9.9% | 9.5% |

Panels were roller-coated with the coating composition and kept for 13 months in seawater at Newton Ferrers, United Kingdom. After 13 months, it appeared that on the panel according to the invention 100% of the coating was still present. In contrast, on the panel provided with the comparative coating composition only 15% of the coating remained. Apparently, the use of zinc pyrithione detrimentally affects the properties of the antifouling coating.

Example 5

This example compares a composition of the invention with a composition which comprises a silyl acrylate resin rather than a copper acrylate resin.

Coating compositions were prepared by high-speed mixing of the constituents mentioned in table 5a.

TABLE 5a

|  | Composition 5 according to the invention | Comparative composition E |
|---|---|---|
| Biocide | 4.0 wt. % Econea | 3.0 wt. % Econea |
| Copper acrylate polymer | 36.1 wt. % | 0 |
| Silyl acrylate polymer[1] | 0 | 47.3 wt. % |
| Solvent | 58.2 wt. % | 48.4 wt. % |
| Other ingredients | 1.7 wt. % | 0.3 wt. % |
| PIGMENT VOLUME CONCENTRATION | 7.0% | 3.8% |

[1]The silyl acylate polymer is Polyace NSP-100 commercially available from Nitto Kasei.

Panels were roller-coated with the coating composition and kept for 8 months in seawater at Newton Ferrers, United Kingdom. After 8 months, the fouling coverage of the panel was determined. Table 5b gives the percentages of the panel which were, respectively clean, covered with slime, covered with weed, and covered with shells.

TABLE 5b

|  | Composition 5 according to the invention | Comparative composition E |
|---|---|---|
| % clean | 100% | 0 |
| % slime | 0 | 70% |
| % weed | 0 | 20% |
| % shell | 0 | 10% |

As can be seen from Table 5b, the composition according to the invention showed 100% clean surface. In contrast, the comparative composition comprising silyl acrylate rather than copper acrylate shows heavy fouling and 0% clean surface.

Example 6

This example compares a composition of the invention with a composition which comprises a zinc acrylate resin rather than a copper acrylate resin.

Coating compositions were prepared by high-speed mixing of the constituents mentioned in table 6a.

TABLE 6a

|  | Composition 6 according to the invention | Comparative composition F |
|---|---|---|
| Biocide | 4.0 wt. % Econea | 4.0 wt. % Econea |
| Copper acrylate polymer | 36.1 wt. % | 0 |
| Zinc acrylate polymer[1] | 0 | 47.3 wt. % |
| Solvent | 58.2 wt. % | 47.9 wt. % |
| Other ingredients | 1.7 wt. % | 0.8 wt. % |
| PIGMENT VOLUME CONCENTRATION | 7.0% | 5.4% |

[1]The zinc acylate polymer is RC4343 commercially available from International paint.

Panels were roller-coated with the coating composition and kept for 8 months in seawater at Newton Ferrers, United Kingdom. After 8 months, the fouling coverage of the panel was determined. Table 6b gives the percentages of the panel which were, respectively clean, covered with slime, covered with weed, and covered with shells.

TABLE 6b

|  | Composition 6 according to the invention | Comparative composition F |
|---|---|---|
| % clean | 80% | 0 |
| % slime | 20% | 0 |
| % weed | 0 | 50% |
| % shell | 0 | 50% |

As can be seen from Table 6b, the composition according to the invention showed 80% clean surface. In contrast, the comparative composition comprising zinc acrylate rather than copper acrylate shows 0% clean surface.

Example 7

This example compares a composition of the invention with a composition which comprises 4,5-dichloro-2-n-octyl-4-isothizolin-3-one (SeaNine 211) as biocide instead of tralopyril.

Coating compositions were prepared by high-speed mixing of the constituents mentioned in table 7a.

TABLE 7a

|  | Composition 7 according to the invention | Comparative composition G |
|---|---|---|
| Biocide | 5.2 wt. % Econea | 5.8 wt. % SeaNine 211 |
| Copper acrylate polymer | 27.6 wt. % | 27.6 wt. % |
| Solvent | 65.3 wt. % | 65.4 wt. % |
| Other ingredients | 1.9 wt. % | 1.3 wt. % |
| PIGMENT VOLUME CONCENTRATION | 12.1% | 16.0% |

Panels were roller-coated with the coating composition and kept for 12 months in seawater at Oyster Bay, N.Y. After 12 months, the fouling coverage of the panel was determined. Table 7b gives the percentages of the panel which were, respectively clean, covered with slime, covered with weed, and covered with shells.

TABLE 7b

|  | Composition 7 according to the invention | Comparative composition G |
|---|---|---|
| % clean | 50% | 0 |
| % slime | 40% | 0 |
| % weed | 10% | 30% |
| % shell | 0 | 70% |

As can be seen from Table 7b, the composition according to the invention showed 50% clean surface. In contrast, the comparative composition comprising SeaNine 211 rather than tralopyril shows 0% clean surface.

The invention claimed is:

1. An antifouling coating composition comprising a copper acrylate polymer, 2-(p-chlorophenyl)-3-cyano-4-bromo-5-trifluoromethyl pyrrole (tralopyril), and solvent, with the coating composition being substantially free of further biocidal compounds, wherein the copper acrylate polymer is present in an amount of 60-99 wt. % and the tralopyril is present in an amount of 0.1-30 wt. %, the weight percentages for copper acrylate polymer and tralopyril being calculated on the dry weight of the coating composition.

2. The antifouling coating composition according to claim 1 comprising 30-80 wt % of solvent, the weight percentage of solvent being calculated on the wet weight of the coating composition.

3. The antifouling coating composition according to claim 1, wherein the amount of tralopyril is at least 0.5 wt. % and/or at most 20 wt. % the weight percentages for tralopyril being calculated on the dry weight of the coating composition.

4. The antifouling coating composition according to claim 1, wherein the coating composition comprises at least 70 wt. % of copper acrylate polymer and/or at most 98 wt. % the weight percentages for copper acrylate polymer being calculated on the dry weight of the coating composition.

5. The antifouling coating composition according to claim 1, wherein the coating composition comprises at least 40 wt. % of solvent and at most 75 wt. %, the weight percentage of solvent being calculated on the wet weight of the coating composition.

6. The antifouling coating composition according to claim 1, wherein the composition comprises 0-15 wt. % of further components, wherein further components are all compounds which are not solvent, copper acrylate polymer, and tralopyril, the weight percentages of further components being calculated on the wet weight of the coating composition.

7. The antifouling coating composition according to claim 1, wherein the coating composition has a pigment volume concentration (PVC) of less than 30%.

8. The antifouling coating composition according to claim 1 wherein the copper acrylate polymer has an acrylic backbone bearing at least one terminal group of the formula:

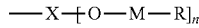

wherein X represents

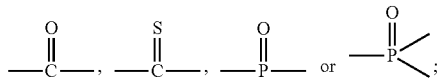

M is copper;
n is an integer of 1 to 2;
R represents an organic residue selected from

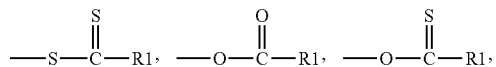

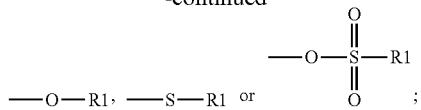

and R1 is a monovalent organic residue.

9. The antifouling coating composition according to claim 8 wherein X represents

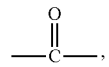

and R represents

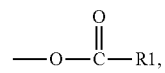

wherein R1 is a monovalent organic residue.

10. A process for protecting a man-made structure immersed in a fouling aquatic environment wherein the structure is coated with an antifouling coating composition according to claim 1.

11. The process according to claim 10, wherein the coating composition is applied through spraying.

12. A man-made structure immersed in a fouling aquatic environment coated with an antifouling coating composition according to claim 1.

13. The man-made structure according to claim 12 that is a ship or boat hull.

14. The man-made structure according to claim 12, wherein the antifouling coating has a thickness after curing of 75 to 150 microns.

15. The antifouling coating composition according to claim 1, wherein the coating composition comprises at least 55 wt. % and at most 65 wt. % of solvent, the weight percentage of solvent being calculated on the wet weight of the coating composition.

16. The antifouling coating composition according to claim 1, wherein the composition comprises 0-5 wt. % of further components, wherein further components are all compounds which are not solvent, copper acrylate polymer, and tralopyril, the weight percentages of further components being calculated on the wet weight of the coating composition.

17. The antifouling coating composition according to claim 1, wherein the coating composition has a pigment volume concentration (PVC) of less than 5%.

18. The man-made structure according to claim 13 that is a ship or boat hull of fiberglass or plastic.

19. The man-made structure according to claim 14, wherein the antifouling coating has a thickness after curing of 90-120 microns.

* * * * *